United States Patent [19]

Rohe et al.

[11] 4,023,958

[45] May 17, 1977

[54] HALOGENATED 4-TRIFLUOROMETHYL-DIPHENYL-ETHER COMPOUNDS AND HERBICIDAL COMPOSITIONS

[75] Inventors: Lothar Rohe, Wuppertal; Jürgen Schramm, Dormagen; Erich Klauke, Odenthal-Hahnenberg; Ludwig Eue; Robert Rudolf Schmidt, both of Cologne, all of Germany

[73] Assignee: Bayer Aktiengesellschaft, Leverkusen, Germany

[22] Filed: Feb. 27, 1976

[21] Appl. No.: 662,067

Related U.S. Application Data

[62] Division of Ser. No. 483,331, June 26, 1974, Pat. No. 3,957,865.

[30] Foreign Application Priority Data

July 3, 1973 Germany .......................... 2333848

[52] U.S. Cl. .......................... 71/103; 260/607 AR
[51] Int. Cl.$^2$ .......................... A01N 9/14
[58] Field of Search ........ 260/607 AR, 609 F, 337; 71/103

[56] References Cited

UNITED STATES PATENTS

| | | | |
|---|---|---|---|
| 3,776,961 | 12/1973 | Theissen | 260/607 AR |
| 3,798,276 | 3/1974 | Bayer | 260/609 F |
| 3,813,444 | 5/1974 | Abe et al. | 260/607 AR |

Primary Examiner—Delbert R. Phillips
Attorney, Agent, or Firm—Burgess, Dinklage & Sprung

[57] ABSTRACT

Halogenated 4-trifluoromethyl-diphenyl-ether compounds of the formula

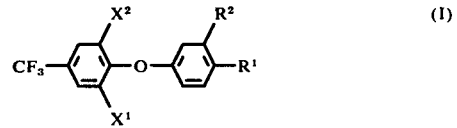

in which
 $R^1$ is alkylthio of from 1 to 4 carbon atoms, alkylsulfinyl or alkylsulfonyl of from 1 to 4 carbon atoms, or aminothiocarbonyl;
 $R^2$ is hydrogen or methyl;
 $X^1$ is halogen; and
 $X^2$ is hydrogen or halogen;

are outstandingly effective as herbicides, particularly as selective herbicides.

17 Claims, No Drawings

HALOGENATED 4-TRIFLUOROMETHYL-DIPHENYL-ETHER COMPOUNDS AND HERBICIDAL COMPOSITIONS

This is a division of application Ser. No. 483,331 filed June 26, 1974 now U.S. Pat. No. 3,957,865 filed 5-18-76.

The present invention relates to certain new halogenated 4-trifluoromethyl-diphenyl-ether copounds, to herbicidal compositions containing them, and to herbicidal applications using them.

It is known that 2,4-dichloro-4'-cyano-diphenyl-ether and 2,4,6-trichloro-4'-cyano-diphenyl ether can be used for combating weeds; see German Offenlegungsschrift (German Published Specification) 1,912,000; 2,4-dichloro-4'-nitro-diphenyl-ether, disclosed in U.S. Pat. No. 3,080,225 and sold under the name Nitrofen, is also known. However, these compounds are not active against all weeds, especially if low amounts and low concentrations are used; for example, they have a low activity against species of Echinochloa, such as *Echinochloa crus galli*, which occurs as a weed in rice, and against species of Eleocharis, such as *Eleocharis palustris*.

The present invention provides halogenated 4-trifluoromethyl-diphenyl-ethers of the formula

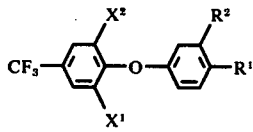   (I)

in which
R¹ is alkylthio of from 1 to 4 carbon atoms, alkylsulfinyl or alkylsulfonyl of from 1 to 4 carbon atoms, or aminothiocarbonyl;
R² is hydrogen or methyl;
X¹ is halogen; and
X² is hydrogen or halogen.

Preferably, X¹ represents chlorine, X² represents hydrogen or chlorine and R¹ represents aminothiocarbonyl or alkylthio of from 1 to 3 carbon atoms, alkylsulfinyl or from 1 to 3 carbon atoms or alkylsulfonyl of from 1 to 3 carbon atoms, especially methylthio, ethylthio, methylsulfinyl, ethylsulfinyl, methylsulfonyl or ethylsulfonyl.

Surprisingly, the halogenated 4-trifluoromethyl-diphenylethers according to the invention display a substantially greater herbicidal action than the compounds known in the art, such as 2,4-dichloro-4'-cyanodiphenyl-ether, 2,4,6-trichloro-4'-cyanodiphenyl-ether and 2,4-dichloro-4'-nitro-diphenyl-ether. The compounds according to the invention thus represent an enrichment of the art.

The invention also provides a process for the production of a halogenated 4-trifluoromethyl-diphenyl-ether of the formula (I) in which
a. a 4-halobenzotrifluoride of the formula

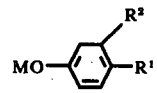   (II)

in which
X¹ and X² have the above-mentioned meanings and Hal represents halogen, is reacted with a phenolate or thiophenolate of the formula

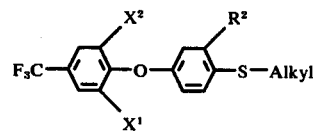   (III)

in which
R¹ and R² have the above-mentioned meanings and
M is an alkali metal, optionally in the presence of an aprotic solvent; or (if R¹ is alkylsulfinyl or alkylsulfonyl)
b. a diphenyl-ether of the formula

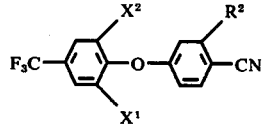   (IV)

in which
X¹, X² and R² have the meanings indicated above, is oxidized with hydrogen peroxide in acid or alkaline solution; or (if R¹ is aminothiocarbonyl)
c. a diphenyl-ether of the formula

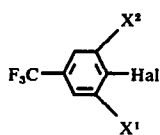   (V)

in which
X¹, X² and R² have the above-mentioned meanings, is reacted with 0,0-diethyl-dithiophosphoric acid in the presence of hydrogen chloride and optionally in the presence of a diluent.

If, in accordance with process variant (a), 3,4,5-trichlorobenzotrifluoride and sodium p-methylsulfonyl-phenolate are used as starting compounds, the course of the reaction can be represented by the following formula scheme:

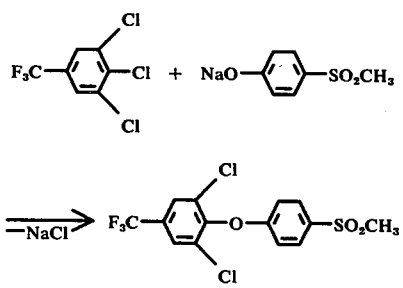

The following formula schemes exemplify process variants (b) and (c), respectively:

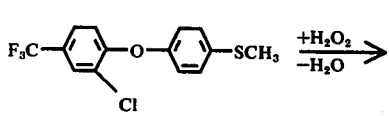

-continued

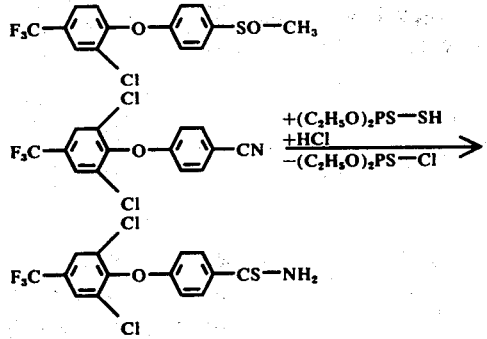

The general formula (II) provides a definition of the 4-halobenzotrifluorides which can be used as starting compounds for variant (a). In this formula, hal preferably represents chlorine. Some of these 4-halobenzotrifluorides are known (see J. Am. Chem. Soc. 57, 2066-2068 (1935) and U.S. Pat. No. 2,654,789); those which are not yet known can be prepared according to methods described in the above literature, by halogenation of benzotrifluorides (such methods are illustrated in the Examples herein).

The general formula (III) provides a definition of the phenolates or thiophenolates used as starting compounds in variant (a). In this formula, M preferably represents sodium or potassium. The sodium phenolates and potassium phenolates and sodium thiophenolates and potassium thiophenolates of the formula (III) are generally known.

All aprotic solvents can be used as diluents in carrying out variant (a). Preferred ones include amides, such as hexamethylphosphoric acid triamide, dimethylformamide or dimethylacetamide and also sulfoxides, such as dimethylsulfoxide, as well as ketones, such as methyl ethyl ketone, and nitriles, such as acetonitrile.

In process variant (a), the reaction temperatures can be varied over a wide range. In general, the reaction temperatures can be varied over a wide range. In general, the reaction is carried out at 40° to 200° C, preferably at 80° to 160° C.

The starting compounds of the formulae (II) and (III) used in process variant (a) are preferably reacted in stoichiometric amounts, but amounts greater or less than this up to 20% can be used without significant losses in yield. The reaction mixture may be worked up in the manner customary in the laboratory.

Process variant (b) belongs to a known type of process, but is new in its particular starting materials. Process variant (c) also belongs to a known type of process (see, on this matter, U.S. Pat. No. 2,822,374); it is illustrated in the Examples herein.

EXAMPLE 1

Preparation of 2,6-dichloro-4-trifluoromethyl-4'-methylthio-diphenyl-ether

Process variant (a):

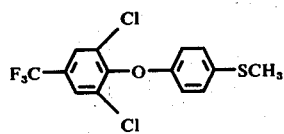

81 g (0.5 mol) of sodium 4-methylthiophenolate were dissolved in 300 ml of dimethylsulfoxide. 125 g (0.5 mol) of 3,4,5-trichlorobenzotrifluoride were added thereto and the mixture was warmed to 140° C for 4 hours. After cooling, the solvent was distilled off almost completely in vacuo, and the residue was poured onto ice water. Twice, 200 ml of methylene chloride were added thereto and the organic phase separated off, washed repeatedly with water, once with 100 ml of 10% strength sodium hydroxide solution and then with water until neutral. After drying over sodium sulfate, the organic phase was freed from the solvent in vacuo; the resulting residue, which was oily but soon crystallized, was recrystallized from methanol. 115 g of 2,6-dichloro-4-trifluoromethyl-4'-methylthio-diphenyl-ether of melting point 48° C were obtained, representing 66% of theory.

EXAMPLE 2

Preparation of 2,6-dichloro-4-trifluoromethyl-3'-methyl-4'-methylthiodiphenyl-ether

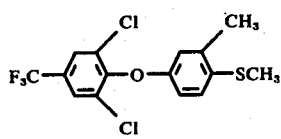

This compound had a refractive index $n_D^{23}$ : 1.5735 and boiling point b.p.$_2$3mm: 168°–170° C was prepared analogously to Example 1.

Preparation of the intermediate:

3,4,5-Trichlorobenzotrifluoride, requires as the intermediate, was obtained in a manner which is in principle known (see J. Am. Chem. Soc. 57, 2066–2068 (1935) and U.S. Pat. No. 2,654,789) by reaction of 4-chlorobenzotrifluoride with chlorine in the presence of 10 mol % of ferric (iron-III) chloride; for this purpose, chlorine was passed into the reaction mixture, at a temperature of 60°–160° C, while stirring and using reflux cooling, until the refractive index of the reaction mixture had risen to $n_D^{20}$ = 1.5025. The mixture was worked up as follows: the catalyst was filtered off and the reaction mixture was distilled through a bridge. The distillate was rectified using a 1 m long silver-jacketed column. In addition to 3,4-dichlorobenzotrifluoride of refractive index $n_D^{20}$ = 1.4758 and boiling point 172°–175° C, a 3,4,5- and 2,4,5-trichlorobenzotrifluoride isomer mixture of refractive index $n_D^{20}$ = 1.5015 was obtained. This mixture was separated by a further vacuum distillation through a silver mirror-coated packed column (1.25 m height, with Wilson glass spiral packings of 3 mm diameter), a magnetic vapor distributor with a time interval switch serving as the column head. A vacuum of 50 mm Hg was applied at the column head; the bath temperature was 142°–150° C and the reflux ratio was 60:1. 3,4,5-Trichlorobenzotrifluoride was then collected at a temperature of 113° C. It was characterized by the NMR spectrum; the compound has a singlet at 7.65 ppm (at 60 MHz, measured in carbon tetrachloride as the solvent).

EXAMPLE 3

Preparation of
2-chloro-4-trifluoromethyl-4'-methylthiodiphenyl-ether

Process variant (a):

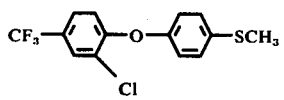
(1)

64.5 g (0.3 mol) of 3,4-dichlorobenzotrifluoride and 48.6 g (0.3 mol) of sodium p-methylmercaptopheno-late were dissolved in 250 ml of dimethylsulfoxide and heated to 135° C for four hours. The solvent was then stripped off in vacuo and the residue was poured into water. The mixture was extracted with 300 ml of methylene chloride. The organic phase was washed with 100 ml of 10% strength sodium hydrochloride solution and then with water. After stripping off the solvent, the residue was distilled.

33 g (31% of theory) of 2-chloro-4-trifluoromethyl-4'-methylthiodiphenyl-ether were obtained as a yellow oil of refractive index $n_D^{22}$ : 1.5662.

EXAMPLE 4

Preparation of
2-chloro-4'-methylsulfinyl-4-trifluoromethyl-diphenyl-ether

Process variant (b):

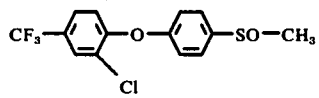
(7)

10 g (0.029 mol) of 2-chloro-4'-methylthio-4-trifluoromethyl-diphenyl-ether (Example 3) were dissolved in 100 ml of toluene and a mixture of 1.5 ml of methanol, 1.5 ml of water, 4.35 g (0.038 mol) of 30% strength hydrogen peroxide and two drops of concentrated sulfuric acid was added and the mixture was warmed to 50° C for 5 hours. After cooling (over ice), the resulting precipitate was filtered off and recrystallized from an ethanol-water mixture. 10 g of 2-chloro-4'-methylsulfinyl-4-trifluoromethyl-diphenyl-ether of melting point 50° C were obtained, representing 99% of theory.

EXAMPLE 5

Preparation of
2,6-dichloro-4-trifluoromethyl-4'-methylsulfinyldiphenyl-ether

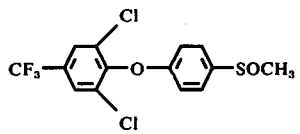
(8)

This compound, which had a melting point 134° C (from ethanol), was prepared analogously to Example 4.

EXAMPLE 6

Preparation of
2-chloro-4'-methylsulfonyl-4-trifluoromethyl-diphenyl-ether

Process variant (b):

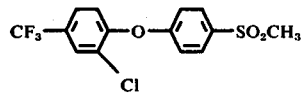
(9)

10 g (0.031 mol) of 2-chloro-4'-methylthio-4-trifluoromethyl-diphenyl-ether (Example 3) were dissolved in 100 ml of ethanol and 11.5 g (0.1 mol) of 30% strength hydrogen peroxide and 1 ml of 6 N sodium hydroxide solution were added. This reaction mixture was kept at 60° C for 3 hours. After cooling over ice water, the resulting precipitate was filtered off and recrystallized from a mixture of ethanol and water. 9.9 g of 2-chloro-4'-methylsulfonyl-4-trifluoromethyl-diphenyl-ether of melting point 44° C were obtained, representing 99% of theory.

EXAMPLE 7

Preparation of
2,6-dichloro-4-trifluoromethyl-4'-methylsulfonyl-diphenyl-ether

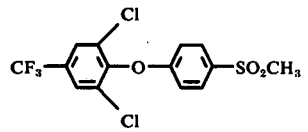
(3)

This compound was prepared analogously to Example 6 from the compound of Example 1. Melting point: 153° C (from ethanol).

EXAMPLE 8

Preparation of
2,6-dichloro-4-trifluoromethyl-4'-aminothiocarbonyl-diphenyl-ether Process variant (c)

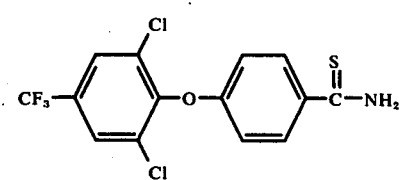
(5)

32.6 g (0.1 mol) of 2,6-dichloro-4'-cyano-4-trifluoromethyl-diphenyl-ether were dissolved in 18.6 g (0.1 mol) of 0.0-diethyldithiophosphoric acid. Dry hydrogen chloride gas was passed into this solution until no further evolution of heat was observed. The reaction mixture was then poured onto water and the product was filtered off, dried and recrystallized from cyclohexane. 15 g of 2,6-dichloro-4-trifluoromethyl-4'-aminothicarbonyl-diphenyl-ether of melting point 153° C were obtained, representing 41% of theory.

The intermediate 2,6-dichloro-4-trifluoromethyl-4'-cyano-diphenyl-ether (melting point 124° C) was prepared analogously to Example 1 by reaction of 3,4,5- trichlorobenzotrifluoride and sodium p-cyanophenolate in dimethylsulfoxide as the solvent.

EXAMPLE 9

Preparation of 2-chloro-4-trifluoromethyl-4'-aminothiocarbonyl-diphenyl-ether 2-Chloro-4-trifluoromethyl-4'-aminothiocarbonyldiphenylether (4) (melting point 106° C) was prepared analogously to Example 8.

The intermediate 2-chloro-4-trifluoromethyl-4'-cyanodiphenyl-ether (melting point 58° C) was prepared analogously to Example 1 from 3,4-dichlorobenzotrifluoride and sodium-4-cyanophenolate in dimethylsulfoxide as the solvent.

The active compounds according to the invention have excellent herbicidal properties and can therefore be used for combating weeds.

Weeds in the broadest sense are plants which grow in locations where they are not desired. As weeds there may be mentioned: dicotyledons, such as mustard (Sinapis), cress (Lepidum), cleavera (Galium), chickweed (Stellaria), camomile (Matricaria), gallant Soldier (Galinsoga), goosefoot (Chenopodium) annual nettle (Urtica) and groundsel (Senecio), and monocotyledons, such as timothy (Phleum), bluegrass (Poa), fescue (Festuca), goosegrass (Eleusine), foxtail (Setaria), ryegrass (Lolium) and barnyard grass (Echinochloa).

The active compounds according to the invention have a very strong influence on plant growth, but in different ways, so that they can be used as selective herbicides. They display particular advantages as selective herbicides in the cultivation of cotton, rice, carrots and cereals (including maize). In higher concentrations (approximately 10 to 20 kg/ha), they can be employed as total weedkillers.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents, and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, e.g. aerosol propellants, such as halogenated hydrocarbons, e.g. freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin, sulfite waste liquors and methyl cellulose.

The active compounds according to the invention can be used as a mixture with other active compounds.

The formulations in general contain from 0.1 to 95 percent by weight of active compound, preferably 0.5 to 90 percent by weight.

The active compounds can be used as such or in the form of their formulations or the application forms prepared therefrom, such as ready-to-use solutions, emulsions, suspensions, powders, pastes and granules. They may be applied in the customary manner, for example by watering, spraying, atomizing, sprinkling and dusting.

They can be applied both post-emergence and pre-emergence; they are preferably applied after emergence of the plants.

The amount of active compound employed can vary within wide recess. It depends essentially on the nature of the desired effect. In general, the amounts used are 0.1 to 25 kg/ha, preferably 0.5 to 10 kg/ha.

The compounds according to the invention also have an insecticidal, acaricidal and fungicidal action which deserves mention.

The invention therefore provides a herbicidal composition containing as active ingredient a compound according to the invention in admixture with a solid or liquefied gaseous diluent or carrier or in admixture with a liquid diluent or carrier containing a surface-active agent.

The invention also provides a method of combating weeds which comprises applying to the weeds or their habitat a compound according to the invention alone or in the form of a composition containing as active ingredient a compound according to the invention in admixture with a diluent or carrier.

The invention also provides means of providing crops protected from damage by weeds by being grown in areas in which, immediately prior to and/or during the time of the growing, a compound according to the invention was applied alone or in admixture with a diluent or carrier. It will be seen that the usual methods of providing a harvested crop may be improved by the present invention.

The compounds according to the invention, and the preparation and use of the compounds according to the invention, are illustrated by the following Examples. The compounds tested in Examples A and B are identified in the following list.

| List of Test Compounds |
|---|
| (1) = 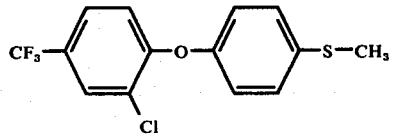 |

-continued

List of Test Compounds (2) = [structure: CF₃, Cl, Cl substituted diphenyl ether with S—CH₃]

(3) = [structure: CF₃, Cl, Cl substituted diphenyl ether with SO₂—CH₃]

(4) = [structure: CF₃, Cl substituted diphenyl ether with C(=S)—NH₂]

(5) = [structure: CF₃, Cl, Cl substituted diphenyl ether with C(=S)—NH₂]

VM-1 (Nitrofen) = [structure: Cl, Cl substituted diphenyl ether with NO₂] (known)

VM-2 = 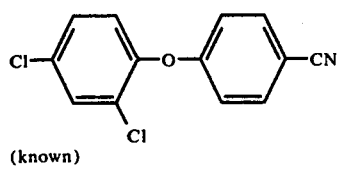 (known) [structure: Cl, Cl substituted diphenyl ether with CN]

List of Test Compounds

VM-3 = [structure: Cl, Cl, Cl substituted diphenyl ether with CN] (known)

Example A

Pre-emergence test
Solvent: 5 parts by weight of acetone
Emulsifier: 1 part by weight of alkylaryl polyglycol ether To produce a suitable preparation of active compound, one part by weight of active compound was mixed with the stated amount of solvent, the stated amount of emulsifier was added and the concentrate was then diluted with water to the desired concentration.

Seeds of the test plants were sown in normal soil and, after twenty-four hours, watered with the preparation of the active compound. It was expedient to keep constant the amount of water per unit area. The concentration of the active compound in the preparation was of no importance, only the amount of active compound applied per unit area being decisive. After three weeks, the degree of damage to the test plants was determined in % damage in comparison to the development of the untreated control.

0% denotes untreated control
100% denotes total destruction

The active compounds, the amounts applied and the results can be seen from Table A.

Table A

Pre-emergence Test

| Active compound | Amount of active compound used, kg/ha | Echino-chlon | Cheno-podium | Lolium | stella ria | Galin soga | Matri-caria | Poly-gonum | Cotton | Wheat | Maize |
|---|---|---|---|---|---|---|---|---|---|---|---|
| (1) | 5 | 100 | 80 | 100 | 80 | 100 | 100 | 80 | 0 | 0 | 0 |
|  | 2.5 | 100 | 80 | 100 | 80 | 100 | 100 | 80 | 0 | 0 | 0 |
|  | 1.25 | 100 | 60 | 80 | 60 | 80 | 100 | 60 | 0 | 0 | 0 |
| (2) | 5 | 100 | 90 | 100 | 100 | 100 | 100 | 80 | 20 | 60 | 20 |
|  | 2.5 | 90 | 70 | 90 | 100 | 90 | 100 | 80 | 0 | 40 | 0 |
|  | 1.25 | 90 | 60 | 80 | 100 | 80 | 100 | 60 | 0 | 20 | 0 |
| (4) | 5 | 100 | 100 | 100 | 100 | 100 | 100 | 100 | 0 | 20 | 0 |
|  | 2.5 | 100 | 100 | 100 | 80 | 100 | 100 | 100 | 0 | 0 | 0 |
|  | 1.25 | 100 | 80 | 80 | 60 | 80 | 80 | 100 | 0 | 0 | 0 |
| (5) | 5 | 100 | 100 | 100 | 100 | 100 | 100 | 100 | 20 | 60 | 20 |
|  | 2.5 | 100 | 100 | 90 | 100 | 100 | 100 | 90 | 0 | 60 | 0 |
|  | 1.25 | 100 | 80 | 80 | 100 | 100 | 100 | 90 | 0 | 20 | 0 |
| VM-1 Nitrofen (known) | 5 | 100 | 60 | 100 | 20 | 90 | 80 | 90 | 40 | 60 | 60 |
|  | 2.5 | 100 | 40 | 90 | 0 | 80 | 80 | 60 | 20 | 40 | 40 |
|  | 1.25 | 100 | 20 | 80 | 0 | 60 | 60 | 40 | 0 | 20 | 40 |
| VM-2 (known) | 5 | 60 | 20 | 20 | 20 | 40 | 40 | 20 | 20 | 0 | 20 |
|  | 2.5 | 60 | 0 | 0 | 20 | 20 | 0 | 0 | 0 | 0 | 0 |
| VM-3 (known) | 5 | 40 | 20 | 20 | 60 | 40 | 40 | 0 | 0 | 20 | 0 |
|  | 2.5 | 20 | 20 | 20 | 40 | 40 | 20 | 0 | 0 | 0 | 0 |

Example B

Post-emergence test
Solvent: 5 parts by weight of acetone
Emulsifier: 1 part by weight of alkylaryl polyglycol ether To produce a suitable preparation of active compound, one part by weight of active compound was mixed with the stated amount of solvent, the stated amount of emulsifier was added and the concentrate was then diluted with water to the desired concentration.

Test plants which had a height of 5–15 cm were sprayed with the preparation of the active compound in such a way as to apply the amounts of active compound per unit area which are indicated in the table..

Depending on the concentration of the spray liquor, the amount of water used was between 1,000 and 2,000 liters/ha. After three weeks, the degree of damage to the plants was determined in % damage in comparison to the development of the untreated control.

0% denotes untreated control
100% denotes total destruction

The active compounds, the amounts used and the results can be seen from Table B.

Table B

| Active compound | Amount of active compound used, kg/ha | Echino- chloa | Cheno- podium | Sina- pis | Galin- soga | Urtica | Cotton | Wheat | Carrots |
|---|---|---|---|---|---|---|---|---|---|
| (2) | 1 | 90 | 80 | 90 | 100 | 100 | 80 | 20 | 0 |
|  | 0.5 | 70 | 60 | 80 | 90 | 100 | 60 | 0 | 0 |
| (3) | 1 | 100 | 90 | 90 | 90 | 100 | 0 | 20 | 0 |
|  | 0.5 | 90 | 80 | 80 | 80 | 100 | 0 | 0 | 0 |
| (5) | 1 | 100 | 90 | 90 | 90 | 100 | 20 | 20 | 0 |
|  | 0.5 | 80 | 80 | 80 | 70 | 100 | 0 | 0 | 0 |
| Nitrofen (known) | 1 | 80 | 60 | 20 | 20 | 100 | 100 | 20 | 0 |
|  | 0.5 | 60 | 60 | 0 | 20 | 100 | 80 | 20 | 0 |
| VM-2 (known) | 1 | 20 | 20 | 40 | 40 | 80 | 40 | 20 | 0 |
|  | 0.5 | 20 | 0 | 20 | 20 | 80 | 40 | 0 | 0 |
| VM-3 (known) | 1 | 0 | 20 | 20 | 40 | 40 | 20 | 20 | 0 |
|  | 0.5 | 0 | 0 | 0 | 0 | 20 | 0 | 0 | 0 |

It will be understood that the specification and examples are illustrative but not limitative of the present invention and that other embodiments within the spirit and scope of the invention will suggest themselves to those skilled in the art.

What is claimed is:

1. Method of combating undesired vegetation, which method comprises applying to such vegetation or its habitat herbicidally effective amounts of a halogenated 4-trifluoromethyldiphenyl-ether compound of the formula

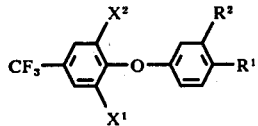

in which
R$^1$ is alkylsulfinyl or alkylsulfonyl of from 1 to 4 carbon atoms;
R$^2$ is hydrogen or methyl;
X$^1$ is halogen; and
X$^2$ is hydrogen or halogen.

2. Method as claimed in claim 1, wherein said compound is applied to weeds growing in a crop cultivation in an amount sufficient to substantially control the weeds without substantially damaging the crops.

3. Method as claimed in claim 2, wherein said crop is cotton.

4. Method as claimed in claim 2, wherein said crop is wheat.

5. Method as claimed in claim 2, wherein said crop is corn.

6. Method as claimed in claim 1 wherein said compound is selected from the group consisting of 2-chloro-4'methylsulfinyl-4-trifluoromethyldiphenylether.

7. Halogenated 4-trifluoromethyldiphenyl ether compound of the formula $$\text{CF}_3\text{—}\underset{\underset{X^1}{|}}{\overset{\overset{X^2}{|}}{\bigcirc}}\text{—O—}\overset{\overset{R^2}{|}}{\bigcirc}\text{—R}^1 \qquad (I)$$

in which
R$^1$ is alkylsulfinyl or alkylsulfonyl of from 1 to 4 carbon atoms;
R$^2$ is hydrogen or methyl;
X$^1$ is halogen; and
X$^2$ is hydrogen or halogen.

8. Halogenated 4-trifluoromethyl-diphenyl-ether compound as claimed in claim 7, wherein R$^2$ is hydrogen.

9. Halogenated 4-trifluoromethyl-diphenyl-ether compound as claimed in claim 7, wherein R$^2$ is methyl.

10. Halogenated 4-trifluoromethyl-diphenyl-ether compound as claimed in claim 7, wherein X$^1$ is chlorine.

11. Halogenated 4-trifluoromethyl-diphenyl-ether compound as claimed in claim 7, wherein X$^2$ is hydrogen.

12. Halogenated 4-trifluoromethyl-diphenyl-ether compound as claimed in claim 7, wherein X$^2$ is chlorine.

13. Halogenated 4-trifluoromethyl-diphenyl-ether compound as claimed in claim 7, designated 2-chloro-4'-methylsulfinyl-4-trifluoromethyl-diphenyl-ether.

14. Halogenated 4-trifluoromethyl-diphenyl-ether compound as claimed in claim 7, designated 2-chloro-4'-methylsulfinyl-4-trifluoromethyl-diphenyl-ether.

15. Halogenated 4-trifluoromethyl-diphenyl-ether compound as claimed in claim 7, designated 2,6-dichloro-4-trifluoromethyl-4'-methylsulfinyldiphenyl-ether.

16. Halogenated 4-trifluoromethyl-diphenyl-ether compound as claimed in claim 7 designated 2-chloro-4'-methylsulfonyl-4-trifluoromethyl-diphenyl-ether.

17. Halogenated 4-trifluoromethyl-diphenyl-ether compound as claimed in claim 7, designated 2,6-dichloro-4-trifluoromethyl-4'-methylsulfonyldiphenyl-ether.

* * * * *